United States Patent [19]

Burnett

[11] 4,153,690

[45] May 8, 1979

[54] **MEDICAMENT DERIVED FROM SOUTHERN WAX MYRTLE (*MYRICA CERIFERA*) FOR ARTHRITIC CONDITIONS**

[76] Inventor: Harvey L. Burnett, 404 Shirley St., DeRidder, La. 70634

[21] Appl. No.: 755,147

[22] Filed: Dec. 29, 1976

[51] Int. Cl.$^2$ ............................................. A61K 35/78
[52] U.S. Cl. ..................................................... 424/195
[58] Field of Search ........................................... 424/195

[56] References Cited

U.S. PATENT DOCUMENTS

| | | | |
|---|---|---|---|
| 81,446 | 8/1868 | Whitlow | 424/195 |
| 92,107 | 6/1869 | Shapley et al. | 424/195 |
| 126,948 | 5/1872 | Frechette | 424/195 |
| 327,603 | 10/1885 | Schwind | 424/195 |
| 3,928,584 | 12/1975 | Hudson | 424/195 |
| 3,932,628 | 1/1976 | Hudson | 424/195 |

OTHER PUBLICATIONS

Roig et al., "Plantas Medicinales", Part I, (1945) Cuba, Ministerio de Agricultura Publication, pp. 127 & 128.
Potter's Cyclopaedia of Botanical Drugs & Preparations (1950), published by Potter & Clark, London, p. 28.
Aetschul, "Drugs & Foods from Little-Known Plants", Harvard U. Press, Camb., Mass. (1973) item 624, p. 48.
Clark, "A Dictionary of Practical Materia Medica", vol. II, Part I, The Homoeopathic Pub. Co. (1902), pp. 515-518.
The National Dispensatory, pp. 927 & 928, published Apr., 1879, Philadelphia.

*Primary Examiner*—Donald B. Moyer
*Attorney, Agent, or Firm*—John F. Sieberth

[57] ABSTRACT

A medicament for treatment of the symptoms of arthritis, rheumatism, and like conditions is provided by subjecting the sap-containing portion of the root of Southern Wax Myrtle (*Myrica cerifera*) to extraction with water at elevated temperature. Internal administration of such preparations has proven effective in alleviating the pain, swelling and suffering caused by arthritis. No adverse side effects have been noted in the test performed to date.

12 Claims, No Drawings

MEDICAMENT DERIVED FROM SOUTHERN WAX MYRTLE (MYRICA CERIFERA) FOR ARTHRITIC CONDITIONS

This invention relates to medicament compositions and to their manufacture and use. More particularly this invention relates to the provision and use of a medicinal agent for alleviating the symptoms of arthritis, rheumatism, and like conditions. Other embodiments, features, characteristics and advantageous aspects of this invention will be apparent from the ensuing description and appended claims.

In accordance with this invention a medicament effective for alleviating the symptoms of arthritis, rheumatism, and like conditions is provided by subjecting the sap-containing portion of the root of Southern Wax Myrtle, Myrica Cerifera, to extraction with a suitable aqueous medium such as water at an elevated temperature. The medicament composition of this invention—-viz, an aqueous extract of the sap-containing portion of the root of Southern Wax Myrtle (Myrica Cerifera) is particularly effective in alleviating the well-known symptoms of arthritis and arthritic rheumatism, notably the pain, swelling and suffering characteristic of these dreaded conditions. In treating such conditions, the medicament or medicinal agent of this invention is administered internally to the afflicted individual. Accordingly, in a further embodiment of this invention there is provided a method for alleviating the symptoms of arthritis, rheumatism, and like conditions which comprises administering to the afflicted individual a small, effective, pharmaceutically acceptable dosage of a medicinal preparation or medicament containing an aqueous extract of the sap-containing portion of the root of Southern Wax Myrtle (Myrica Cerifera).

The sequence used in the manufacture of the medicament of this invention normally involves first removing the protective bark or covering of the root of the Southern Wax Myrtle, such as by scraping or peeling. In this way the tender, fibrous, sappy portion of the root normally covered by this bark is exposed for use in the extraction procedure. Next the tender, fibrous, sappy portion may be scraped away from the inner woody core or body of the roots or, alternatively, the peeled roots may be chopped or otherwise suitably comminuted or sub-divided into small pieces for use in the extraction or leaching step. In the latter case the feed material will of course comprise both the tender, fibrous, sappy portion of the root as well as the inner woody core or body of the root.

The sap-containing portion of the Myrica Cerifera is thereupon subjected to extraction with water at an elevated temperature. Temperatures falling in the range of from about 150–175° F. up to the boiling point of the aqueous extraction system at the prevailing pressure are generally satisfactory. In conducting the extraction operation it is possible to utilize closed reaction vessels whereby the extraction may be performed under super-atmospheric pressure sufficient to maintain the aqueous extractant in the liquid phase. Thus in an appropriately designed closed reaction vessel temperatures as high as about 450° F. may be utilized. However, generally speaking it is preferred to simply conduct the extraction operation in a simple vat or other container open to the atmosphere containing a suitable quantity of the aqueous extraction liquor and the sap-containing portion of the Myrica Cerifera root. In such case the temperature of the system will normally be in the order of about 212° F., i.e., the normal boiling point of the aqueous system at the prevailing atmospheric pressure. In short, it is preferred to conduct the extraction process at or near the boiling point of water at atmospheric pressure.

Although considerable variation is permissible, the extraction system will generally contain from about two to about ten fluid ounces of water per ounce (by weight) of the fibrous, sap-containing portion of the Southern Wax Myrtle being extracted or leached. While greater or lesser proportions of water may be utilized, proportions within the foregoing range are efficacious in that the resultant extracts contain concentrations of the medicament in proximity to the desired dosage forms for administration to afflicted individuals. Accordingly it is unnecessary when using such proportions to make excessively large adjustments in the concentration of the resultant aqueous extract. A particularly preferred proportion involves use of about six fluid ounces of water per ounce (by weight) of the sap-containing portion of the Myrica Cerifera root. Naturally, if the woody core of the root is also present, the weight thereof should be taken into consideration when adjusting the proportions of the materials being fed to the extraction system.

Preferably pure water is used although other suitable pharmaceutically acceptable ingredients may be present in the aqueous extraction medium as fed to or used in the extraction vessel or apparatus. Thus for example the aqueous system may contain suitable quantities of such materials as preservatives or antioxidants, extraction aids, synergists, sweeteners and the like. Examples of such materials are calcium propionate, sodium nitrite, ethanol, glycerine, ethylenediamine tetraacetic acid, tocopherol, tannin, sorbitol, sugar, saccharin and the like.

It is desirable, particularly when performing the extraction on a relatively large scale, to stir or otherwise suitably agitate the contents of the extraction vessel.

Extraction times in the order of from about eight to about fifteen minutes are most satisfactory when performing the extraction with boiling water at atmospheric pressure. When performing the extraction at temperatures above about 212° F. under super-atmospheric pressure, extraction times will generally be somewhat shorter. Conversely when performing the extraction at below about 212° F. somewhat longer extraction periods are desirable in some cases. During the course of this extraction procedure the color of the aqueous system will be changing from a light brown or tan coloration to a dark brown coloration. When the aqueous system reaches a coloration resembling that of iced tea the concentration of the medicament in the water is within the preferred range and thus the extraction procedure may be terminated at this point, if desired.

The aqueous extract is subjected to filtration, straining, centrifugation or the like while hot in order to remove residual particulate matter. Thereupon the clear liquid is allowed to cool to room temperature. At that point there is a tendency for a material of a waxy or resinous consistency to form as a separate phase within the aqueous phase and this waxy or resinous finely divided solid tends to settle to the bottom of the container. After the system has reached room temperature and the solid has settled in the container, then it is most preferable to visually inspect the color of the clear supernatant liquid material. If at that point it has a color essentially resembling that of iced tea, the medicament is of suitable strength for packaging, storage and direct administration to afflicted individuals. On the other hand if the color of the clear supernatant liquid material is significantly lighter than the color of iced tea, it is generally desirable to concentrate the system either by boiling off excess water or by using the dilute system as the extraction medium for additional sap-containing portions of the Myrica Cerifera root. Conversely if the color of the clear supernatant liquid is found excessively darker than iced tea coloration, the solution may contain an unnecessarily high concentration of the medicament of this invention. In such a case it is generally desirable to dilute the system with water until the desired color is achieved before packaging the preparation for distribution to the consumer. It will of course be understood that the precise coloration and concentration of the medicament in the aqueous solution is not critical to the practice or the efficacy of this invention since the material is effective within a reasonably broad range of proportions. Further no indications have been found in the development of this invention to date which would indicate that there is any danger of any adverse effect produced from use of higher dosages of the medicament. Accordingly, the adjustment of the coloration to resemble that of iced tea is merely for the purpose of achieving proportions which have been found in actual practice to give excellent results in the treatment of arthritic conditions. Thus the color or optical characteristics of the clear solution serve as a convenient indicator that there is present in the aqueous solution a suitable pharmaceutically effective amount of the medicament.

When packaging the medicament compositions it is desirable to agitate, stir or shake the aqueous mixture to insure that the waxy, resinous, separate phases are substantially uniformly dispersed in the aqueous phase so that the individual containers will receive proportionate quantities of this solid phase as well as the liquid phase. When the product is administered to the afflicted individual, the contents of the container should be shaken before use.

Dosages for administration to an afflicted individual are of course subject to variation depending upon such factors as the severity of the condition being treated, the rapidity of the alleviation desired and above all the professional judgment of any dispensing physician who may prescribe its use. In the experimentations performed to date on this invention it has been found that excellent results have been achieved when the afflicted individual consumes two fluid ounces of the well-shaken medicament (prepared as above-described; iced tea coloration) followed by a period of one hour or so after which two additional fluid ounces are consumed. It is believed that wherever possible the afflicted individual should avoid use of other types of medication during a period of at least eight hours or so prior to the administration of the medicament of this invention. In this way the action of the aqueous extract of the sap-containing portion of the Southern Wax Myrtle in alleviating pain and other adverse symptoms of arthritis and arthritic rheumatism will not be subject to potential interference or impairment by other pharmaceutical agents, drugs, stimulants or the like.

In actual practice it will generally be found that within about eight hours after the administration of the medicament of this invention in the manner described above, the severe pain and suffering normally associated with advanced cases of arthritis will have vanished or at least substantially subsided. In addition the excessive swelling and disfigurement associated with advance cases of arthritis will usually be alleviated within about forty-eight hours after such administration. With a suitable regimen of exercise, the mobility of arthritically affected joints may be at least partially restored after use of the medicament of this invention. No adverse side effects have been noted in the test work performed to date.

The following are illustrations of the practice and advantages of this invention.

EXAMPLE I

In this instance the afflicted individual was a woman in her sixties with a severe case of arthritis. She was experiencing severe pain and swelling in the right shoulder, right elbow and excruciating pain in the right hand, especially the thumb, index and middle fingers. The slightest touch of these fingers such as by a blanket was found almost unbearable. The sap-containing portion of the Southern Wax Myrtle (Myrica Cerifera) was extracted with boiling water in an open vessel in proportions of about six fluid ounces of water per ounce by weight of the sap-containing portion of the root. The medicament had the color approximating that of iced tea and contained the separate waxy or resinous, finely divided solid phase which was suspended within the body of the liquid by shaking the preparation immediately prior to administration. A dosage of about two fluid ounces was ingested orally followed by a second ingestion of about two fluid ounces after an intervening period of about one hour. In about eight hours the afflicted individual reported that the pain had completely left her. In about two weeks all of the adverse symptoms of the arthritis had disappeared. No further medication for the condition was required or utilized. Throughout a period of about two and one half to three years subsequent to the ingestion of the foregoing two doses of the preparation there has been no reoccurence of the pain or swelling in any of the affected portions of the individual. The present mobility of the previously affected joints in the shoulder, arm and hand is considered normal.

EXAMPLE II

In this instance the afflicted individual was a man in his sixties who had experienced a severe pain and swelling in his left shoulder, left arm, and left hand (all fingers). The medicament of the present invention was prepared and administered in the manner described in the previous example. He found that the pain of the arthritic condition left him in about seven hours after consumption of the second dosage of two ounces. Within ten days thereafter all symptoms of his arthritic condition had disappeared. Since that time a period of two years has elapsed and there has been no reoccurence of the affliction or the symptoms thereof. No additional medication for the condition has been required or used.

EXAMPLE III

A woman in her fifties suffering a very severe case of arthritis in both of her arms and legs employed the medicament of this invention. Prior to taking the preparation her condition was so severe that both legs required braces and she was ambulatory only with the aid of two crutches. As in the previous Examples a total of four fluid ounces of the medicament prepared as described (iced tea coloration) was ingested in the manner described. She reported that within eight hours all of the pain and suffering that she had been experiencing as a result of her arthritis had disappeared. With the aid of exercise over a period of eight days following utilization of the medicament she was able to discard her braces and crutches. In fact within two weeks after taking the four ounces of the medicament she was able to drive an automobile and carry on her normal business activities without pain.

The foregoing Examples illustrate at firsthand the actual results which have been achieved when utilizing this invention. A number of other persons have tested the medicament on a experimental basis and in all cases alleviation of adverse symptoms of arthritis and arthritic rheumatism have been experienced. In no case has any adverse side effect been observed. In all instances the foregoing beneficial results were achieved by use of a total of approximately four fluid ounces of the medicament, except in one instance where a woman in her thirties required a third dosage of two fluid ounces approximately two months after the two initial two ounce dosages in order to completely relieve the arthritic pain she had been experiencing in her shoulder.

The chemical composition of the medicament of this invention is not known with any particularity. Samples of the material have been subjected to chemical analyses and the following results and observations were made:
   a. X-ray analysis showed no heavy metals, such as mercury, lead, iron, etc., were present in detectible quantity.
   b. Nuclear magnetic resonance spectroscopy showed the presence of chemical groups which could be present in volatile oils, longchain carbon compounds, and aromatics.
   c. Chromatography showed the presence of at least three components, probably volatile oils.
   d. Other tests showed that the solution was acidic, probably due to long-chain organic acids such as tetradecanoic acid (myristic acid) or other organic acids such as gallic or tannic acids; that amino acids were present; and that tannins and phenolic compounds were probably present.
   e. The presence of free alkaloids or cyanides was not detected.

Hence it had been postulated that the material contains, interalia, wax, resins, organic acids (such as tannic, gallic, and and myristic), starch or other simpler carbohydrates, volatile oils, gum, and amino acids. The question of what components or factors in the medicament are responsible for its efficacy remains unanswered. In this connection, it has not been determined whether it is necessary for the afflicted individual to consume the suspended waxy or resinous solids together with the liquid phase of the aqueous extract or whether the benefits of this invention will result from ingestion of the clear solution absent the solids.

From the foregoing it can been seen that this invention is susceptible to considerable variation and latitude in its practice and in order to achieve the optimum advantageous benefits provided thereby. Accordingly this invention is not intended to be unduly limited by the description herein set forth. Rather this invention is intended to extend to the scope of the ensuing claims and the equivalents thereof.

I claim:

1. A process of preparing a medicament for alleviating arthritic pain which comprises
   a. removing the protective bark from the root of Southern Wax Myrtle (Myrica Cerifera);
   b. subjecting the resulting exposed sap-containing portion of said root to extraction with water at an elevated temperature so that the water leaches and dissolves components from the exposed sapcontaining portion of said root as evidenced by a darkening of the coloration of the resulting aqueous extraction solution; and
   c. terminating the extraction when said solution possesses a brown coloration.

2. The process of claim 1 wherein extraction is performed with boiling water at substantially atmospheric pressure.

3. The process of claim 1 wherein extraction is performed for a period of from about eight to about fifteen minutes, the proportions of said sap-containing portion and water being such that at the end of this time the clear supernatant liquid at room temperature has the color approximating that of iced tea.

4. The process of claim 1 wherein extraction is performed in an extraction system containing from about two to about ten fluid ounces of water per ounce by weight of tender, fibrous, sap-containing portion of the root of Southern Wax Myrtle (Myrica Cerifera).

5. The process of claim 4 wherein extraction is performed with boiling water at substantially atmospheric pressure for a period of about eight to about fifteen minutes.

6. The process of claim 1 wherein said sap-containing portion used in the extraction is prepared by removing the protective bark of the root of the Southern Wax Myrtle (Myrica Cerifera) and then separating from the inner woody core of said debarked root the fibrous, sappy portion thereof.

7. A medicament composition for alleviating arthritic pain which comprises an aqueous extract of the sap-containing portion of the root of Southern Wax Myrtle (Myrica Cerifera) which has been produced by
   a. removing the protective bark from the root of Southern Wax Myrtle (Myrica Cerifera);
   b. subjecting the resulting exposed sap-containing portion of said root to extraction with water at an elevated temperature so that the water leaches and dissolves components from the exposed sap-containing portion of said root as evidenced by a darkening of the coloration of the resulting aqueous extraction solution; and
   c. terminating the extraction when said solution possesses a brown coloration.

8. A composition in accordance with claim 7, wherein said aqueous extract comprises an aqueous solution having a brown coloration comparable to that of iced tea.

9. A method for alleviating arthritic pain which comprises administering to the afflicted individual a small, effective, pharmaceutically acceptable, orally ingestible dosage of a medicament containing an aqueous extract of the sap-containing portion of the root of Southern Wax Myrtle (Myrica Cerifera), said dosage being effective for alleviating said arthritic pain.

10. A method in accordance with claim 9 further characterized in that said aqueous extract has a brown coloration comparable to that of iced tea.

11. A method in accordance with claim 9 further characterized in that said aqueous extract has been produced by
 a. removing the protective bark from the root of Southern Wax Myrtle (Myrica Cerifera);
 b. subjecting the resulting exposed sap-containing portion of said root to extraction with water at an elevated temperature so that the water leaches and dissolves components from the exposed sap-containing portion of said root as evidenced by a darkening of the coloration of the resulting aqueous extraction solution; and
 c. terminating the extraction when said solution possesses a brown coloration.

12. A method in accordance with claim 11 further characterized in that said extraction was performed in boiling water in proportions of from about two to about ten fluid ounces of water per ounce by weight of the sap-containing portion of said root.

* * * * *